US010231611B2

(12) United States Patent
Li

(10) Patent No.: US 10,231,611 B2
(45) Date of Patent: Mar. 19, 2019

(54) ORAL ENDOSCOPE DETECTION SYSTEM AND DETECTION METHOD THEREOF

(71) Applicant: Xiang Li, Sichuan (CN)

(72) Inventor: Xiang Li, Sichuan (CN)

( * ) Notice: Subject to any disclaimer, the term of this patent is extended or adjusted under 35 U.S.C. 154(b) by 78 days.

(21) Appl. No.: 15/322,715

(22) PCT Filed: Jul. 28, 2016

(86) PCT No.: PCT/CN2016/092017
§ 371 (c)(1),
(2) Date: Dec. 28, 2016

(87) PCT Pub. No.: WO2017/032200
PCT Pub. Date: Mar. 2, 2017

(65) Prior Publication Data
US 2017/0209035 A1 Jul. 27, 2017

(30) Foreign Application Priority Data
Aug. 27, 2015 (CN) .......................... 2015 1 0533307

(51) Int. Cl.
*A61B 1/04* (2006.01)
*A61B 1/24* (2006.01)
(Continued)

(52) U.S. Cl.
CPC ............ *A61B 1/24* (2013.01); *A61B 1/00009* (2013.01); *A61B 1/00045* (2013.01);
(Continued)

(58) Field of Classification Search
CPC ......... A61B 1/24; A61B 1/04; A61B 1/00045; A61B 1/00114; A61B 1/00009; G02B 23/2484; H04N 5/23293; H04N 5/38
See application file for complete search history.

(56) References Cited

U.S. PATENT DOCUMENTS 6,483,535 B1 * 11/2002 Tamburrino ....... A61B 1/00163
348/345
7,217,241 B2 * 5/2007 Guenier ............. A61B 1/00149
433/30
(Continued)

FOREIGN PATENT DOCUMENTS

CN 101494043 A 7/2009
CN 101730498 A 6/2010
(Continued)

*Primary Examiner* — Sathyanaraya V Perungavoor
*Assistant Examiner* — Howard D Brown, Jr.
(74) *Attorney, Agent, or Firm* — Novick, Kim & Lee, PLLC; Allen Xue

(57) ABSTRACT

The invention discloses an oral endoscope detection system and a detection method thereof. The oral endoscope detection system comprises an insertion portion, a camera unit arranged in the insertion portion, a displacement information acquisition module, an operation mode setting module, a signal transmission module, an operation unit connected with the insertion portion, an image control processing module and a display device. An image displayed on the display device is a positive visual image of a subject part by using the invention, so that the operator can better operate a subject oral cavity to avoid the situation that the operator cannot make correct judgment because detection images taken by oral endoscopes in the prior art are upside down or skew.

11 Claims, 6 Drawing Sheets

(51) Int. Cl.
*A61B 1/00* (2006.01)
*G02B 23/24* (2006.01)
*H04N 5/232* (2006.01)
*H04N 5/38* (2006.01)
*A61B 5/00* (2006.01)
*H04N 5/225* (2006.01)

(52) U.S. Cl.
CPC ............ *A61B 1/00114* (2013.01); *A61B 1/04* (2013.01); *G02B 23/24* (2013.01); *G02B 23/2484* (2013.01); *H04N 5/23245* (2013.01); *A61B 5/0079* (2013.01); *H04N 5/23293* (2013.01); *H04N 5/38* (2013.01); *H04N 2005/2255* (2013.01)

(56) References Cited

U.S. PATENT DOCUMENTS

| | | | |
|---|---|---|---|
| 2003/0107652 A1* | 6/2003 | Williams | A61B 1/00177 348/207.99 |
| 2003/0228553 A1* | 12/2003 | Mandelkern | A61B 1/00016 433/29 |
| 2004/0152037 A1* | 8/2004 | Schick | A61B 1/24 433/29 |
| 2009/0087050 A1* | 4/2009 | Gandyra | G01B 11/03 382/128 |
| 2010/0189341 A1* | 7/2010 | Oota | A61B 1/0019 382/154 |
| 2012/0295217 A1* | 11/2012 | Kim | A61B 5/0062 433/29 |
| 2013/0184532 A1* | 7/2013 | Goldfarb | A61B 1/00183 600/171 |

FOREIGN PATENT DOCUMENTS

| | | |
|---|---|---|
| CN | 201551343 U | 8/2010 |
| JP | H11-89793 A | 4/1999 |
| WO | 2007063980 A1 | 6/2007 |
| WO | 2011118839 A1 | 9/2011 |
| WO | 2013008097 A1 | 1/2013 |

* cited by examiner

ORAL ENDOSCOPE DETECTION SYSTEM AND DETECTION METHOD THEREOF

FIELD OF THE INVENTION

The invention belongs to the technical field of endoscopes, in particular to an oral endoscope detection system having a special image processing function and a detection method thereof.

DESCRIPTION OF THE RELATED ART

In recent years, endoscopes built with camera units in insertion portions are widely used in the detection of oral cavities. Oral endoscopes in the prior art have to continuously change positions during use, and images acquired by such endoscopes will turn upside down or rotate as the insertion portions turn upside down or rotate, as a result, it is difficult for operators to accurately operate oral cavities. In order to keep image display accuracy, users have to continuously adjust the positions of the insertion portions, which is troublesome and makes trouble for subjects.

SUMMARY OF THE INVENTION

In order to solve the problem, the invention provides an oral endoscope detection system comprising an insertion portion, a camera unit arranged in the insertion portion, a displacement information acquisition module, an operating mode setting module, a signal transmission module, an operation unit connected with the insertion portion, an image control processing module and a display device;
the camera unit, the displacement information acquisition module, the operating mode setting module and the signal transmission module being connected with the image control processing module, and the display device being connected with the signal transmission module;
the insertion portion being used to insert into a subject oral cavity;
the camera unit being used to acquire image information of the subject oral cavity, and transmit the image information to an image information processing module;
the operating mode setting module being used for a user to select a mode for private purpose or mode for other purpose;
in the mode for private purpose, the user detecting the oral cavity independently, and in the mode for other purpose, the user detecting the subject oral cavity against the subject;
the image control processing module being embedded with information of standard initial attitude coordinate systems of both modes;
the information of the standard initial attitude coordinate system of the mode for private purpose being described as follows: the straight-line direction from the left shoulder to the right shoulder of the user is the forward direction of X axis; the direction in perpendicular to X axis and in the same direction as the image taking direction is the forward direction of Z axis; the direction in perpendicular to Z axis and X axis respectively and toward the upper part of the oral cavity is the forward direction of Y axis, and the origin being located on a connecting line between the operation unit and the camera unit;
the information of the standard initial attitude coordinate system of the mode for other purpose being described as follows: the straight-line direction from the left shoulder to the right shoulder of the subject is the forward direction of X axis; the direction in perpendicular to X axis and in the same direction as the image taking direction is the forward direction of Z axis; the direction in perpendicular to Z axis and X axis respectively and toward the upper part of the subject oral cavity is the forward direction of Y axis, and the origin being located on a connecting line between the operation unit and the camera unit;
during movement of the camera unit, the standard initial attitude coordinate system of the mode for private purpose moving integrally as a housing moves to become a standard attitude coordinate system of the mode for private purpose; and the standard initial attitude coordinate system of the mode for other purpose moving integrally as the housing moves to become a standard attitude coordinate system of the mode for other purpose;
the image control processing module controlling the camera unit, and making correction based on the operating mode selected by the user and information of the corresponding standard initial coordinate system as well as rotation angle and rotation rate acquired by the displacement information acquisition module;
the displacement information acquisition module being used to detect the rotation angle and rotation rate of the connecting line between the camera unit and the operation unit relative to rotation of the standard attitude coordinate system from X axis to Y axis during shooting of each frame of image;
the signal transmission module being connected with the image control processing module for signal transmission; and
the display device being used to display corrected images.
Further, in the mode for private purpose, the step of correcting images by the image control processing module comprises:
step 1: correcting acquired images at the same rotation rate and opposite rotation angles; and
step 2: carrying out 180° mirroring rollover on the corrected images in the step 1.
Further, in the mode for other purpose, the image control processing module makes correction to images in the follow way: correcting acquired images at the same rotation rate and rotation angle.
Further, the signal transmission module comprises a wireless transceiver component or a WIFI transceiver component or a Bluetooth component or a USB wired transmission component.
Further, the displacement information acquisition module is an acceleration sensor and/or angular velocity sensor and/or gyroscope and/or gravity sensor.
Further, the central axis of the insertion portion is a connecting line between the camera unit and the operation unit.
A detection method of the oral endoscope detection system, characterized by comprising the following steps:
S1: selecting an operating mode by using the operating mode setting module by the user;
S2: aligning the endoscopic camera unit with the subject oral cavity, acquiring image information by the camera unit, and detecting the rotation angle and rotation rate of the connecting line between the camera unit and the operation unit relative to rotation of the standard attitude coordinate system from X axis to Y axis by the displacement information acquisition module during shooting of each frame of image;
S3: transmitting the image information of each frame of image and the corresponding rotation angle and rotation rate to the image control processing module;
S4: the image control processing module corrects the images;

in the mode for private purpose, the step of correcting images by the image control processing module comprises:
step 1: correcting acquired images at the same rotation rate and opposite rotation angles; and
step 2: carrying out 180° mirroring rollover on the corrected images in the step 1;
in the mode for other purpose, the image control processing module makes correction to images in the follow way: correcting acquired images at the same rotation rate and rotation angle; and
S5: displaying the images by the display device.

The invention has the following beneficial effects:
The invention creatively solves the problem that it is difficult to positively display images acquired by oral endoscopes to subjects in the prior art, improving the operation accuracy of oral cavities, and improving the operation flexibility and shape design flexibility of endoscopes while ensuring the image display accuracy, thus the invention has good application values.

DESCRIPTION OF THE PREFERRED EMBODIMENT

Figure 1:
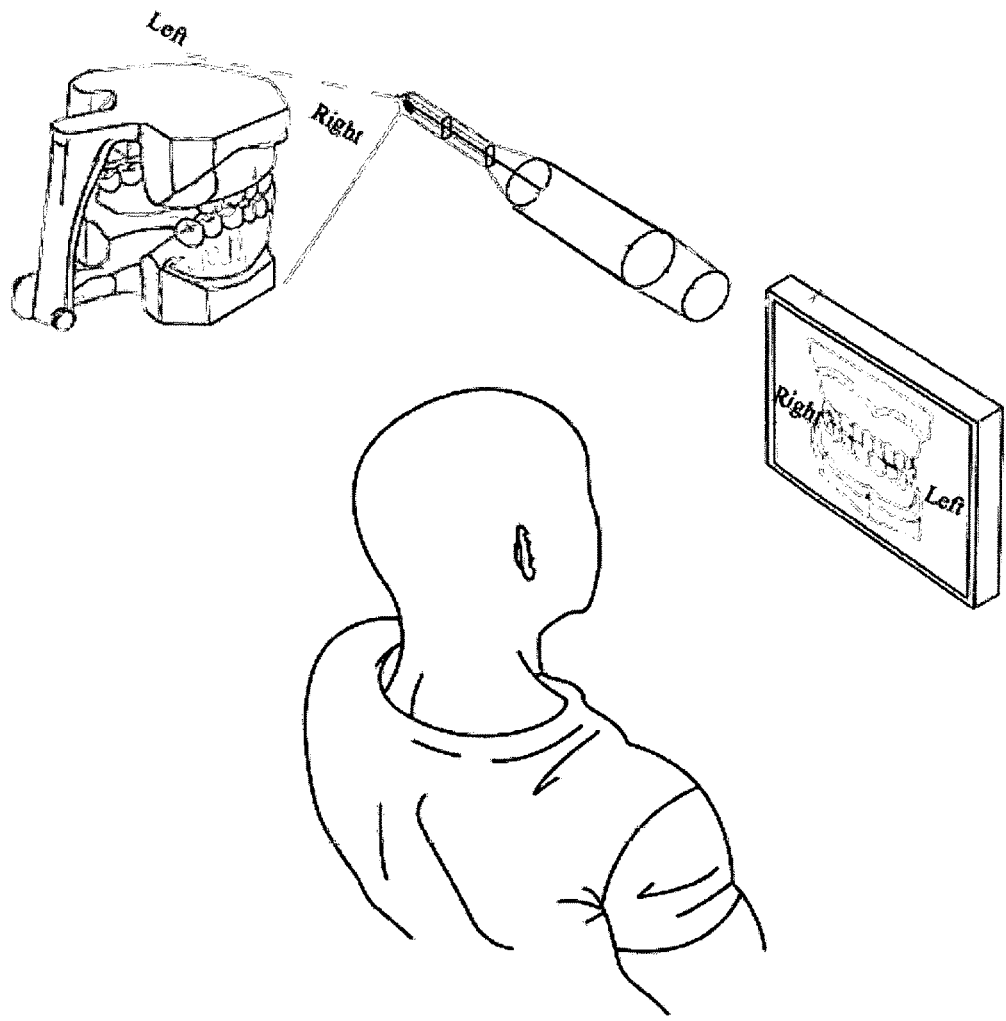
FIG. 1 is a sketch to use an endoscope for private purpose in the prior art.

The design concept of the invention is to provide an endoscope which can be provided with an insertion portion to be inserted into a human oral cavity and a handheld part for an operator. In the event of any attitude change of the insertion portion in the human oral cavity, an image displayed on the display device is a positive visual image of a subject part, so that the operator can better operate the subject oral cavity to avoid the situation that the operator cannot make correct judgment because detection images taken by oral endoscopes in the prior art are upside down or skew.

The oral endoscope detection system of the invention comprises an insertion portion, a camera unit arranged in the insertion portion, a displacement information acquisition module, an operating mode setting module, a signal transmission module, an operation unit connected with the insertion portion, an image control processing module and a display device.

The insertion portion is used to insert into a subject oral cavity.

The camera unit is used to acquire image information of the subject oral cavity, and transmit the image information to an image information processing module.

The operating mode setting module is used for a user to select a mode for private purpose or mode for other purpose; in the mode for private purpose, the user detects the oral cavity independently, and in the mode for other purpose, the user detects the subject oral cavity against the subject. The operating mode setting module can take the form as follows: the software is arranged in the image control processing module, and the operation control part is arranged on the endoscope housing, or the operating mode is switched by using virtual buttons.

The image control processing module is embedded with information of standard initial attitude coordinate systems of both modes.

The information of the standard initial attitude coordinate system of the mode for private purpose is described as follows: the straight-line direction from the left shoulder to the right shoulder of the user is the forward direction of X axis; the direction in perpendicular to X axis and in the same direction as the image taking direction is the forward direction of Z axis; the direction in perpendicular to Z axis and X axis respectively and toward the upper part of the oral cavity is the forward direction of Y axis, and the origin being located on a connecting line between the operation unit and the camera unit.

The information of the standard initial attitude coordinate system of the mode for other purpose is described as follows: the straight-line direction from the left shoulder to the right shoulder of the subject is the forward direction of X axis; the direction in perpendicular to X axis and in the same direction as the image taking direction is the forward direction of Z axis; the direction in perpendicular to Z axis and X axis respectively and toward the upper part of the subject oral cavity is the forward direction of Y axis, and the origin being located on a connecting line between the operation unit and the camera unit.

During movement of the camera unit, the standard initial attitude coordinate system of the mode for private purpose moves integrally as a housing moves to become a standard attitude coordinate system of the mode for private purpose; and the standard initial attitude coordinate system of the mode for other purpose moves integrally as the housing moves to become a standard attitude coordinate system of the mode for other purpose.

The setting mode of the coordinate systems ensures that the coordinate systems are only correlated to the subject oral cavity at any time, and has nothing to do with the attitude of the user or the subject, improving the operation flexibility of the endoscope.

The design of the coordinate systems has nothing to do with the shape of the endoscope, but is only associated with the relative position of the camera and the handheld part, which improves the shape design flexibility of the endoscope, and provides convenience for the displacement information acquisition module to acquire information. Preferably, the central axis of the insertion portion is a connecting line between the camera unit and the operation unit.

The displacement information acquisition module is used to detect the rotation angle and rotation rate of the connecting line between the camera unit and the operation unit relative to rotation of the standard attitude coordinate system from X axis to Y axis during shooting of each frame of image. The module can be set as an acceleration sensor and/or angular velocity sensor and/or gyroscope and/or gravity sensor.

The image control processing module controls the camera unit, and makes correction by the following method based on the operating mode selected by the user and information of the corresponding standard initial coordinate system as well as rotation angle and rotation rate acquired by the displacement information acquisition module:

in the mode for private purpose, the step of correcting images by the image control processing module comprises: step 1: correcting acquired images at the same rotation rate and opposite rotation angles; and
step 2: carrying out 180° mirroring rollover on the corrected images in the step 1.

In the mode for other purpose, the image control processing module makes correction to images in the follow way: correcting acquired images at the same rotation rate and rotation angle.

The signal transmission module is connected with the image control processing module for signal transmission. The signal transmission module further comprises a wireless transceiver component or a WIFI transceiver component or a Bluetooth component or a USB wired transmission component besides existing necessary transmission circuits.

The display device is used to display corrected images. The display device can be a mobile phone, a computer or a tablet, and shall face the user or the subject directly.

The detection steps of the invention are described as follows.

S1: selecting an operating mode by using the operating mode setting module by the user;

S2: aligning the endoscopic camera unit with the subject oral cavity, acquiring image information by the camera unit, and detecting the rotation angle and rotation rate of the connecting line between the camera unit and the operation unit relative to rotation of the standard attitude coordinate system from X axis to Y axis by the displacement information acquisition module during shooting of each frame of image;

S3: transmitting the image information of each frame of image and the corresponding rotation angle and rotation rate to the image control processing module;

S4: correcting the images by the image control processing module;

in the mode for private purpose, the step of correcting images by the image control processing module comprises: step 1: correcting acquired images at the same rotation rate and opposite rotation angles; and
step 2: carrying out 180° mirroring rollover on the corrected images in the step 1;

in the mode for other purpose, the image control processing module makes correction to images in the follow way: correcting acquired images at the same rotation rate and rotation angle; and S5: displaying the images by the display device.

The transmission of all signals in the above process is completed by the signal transmission module.

The effects of the invention will be further described in combination with FIG. 1 through FIG. 6.

Figure 2:
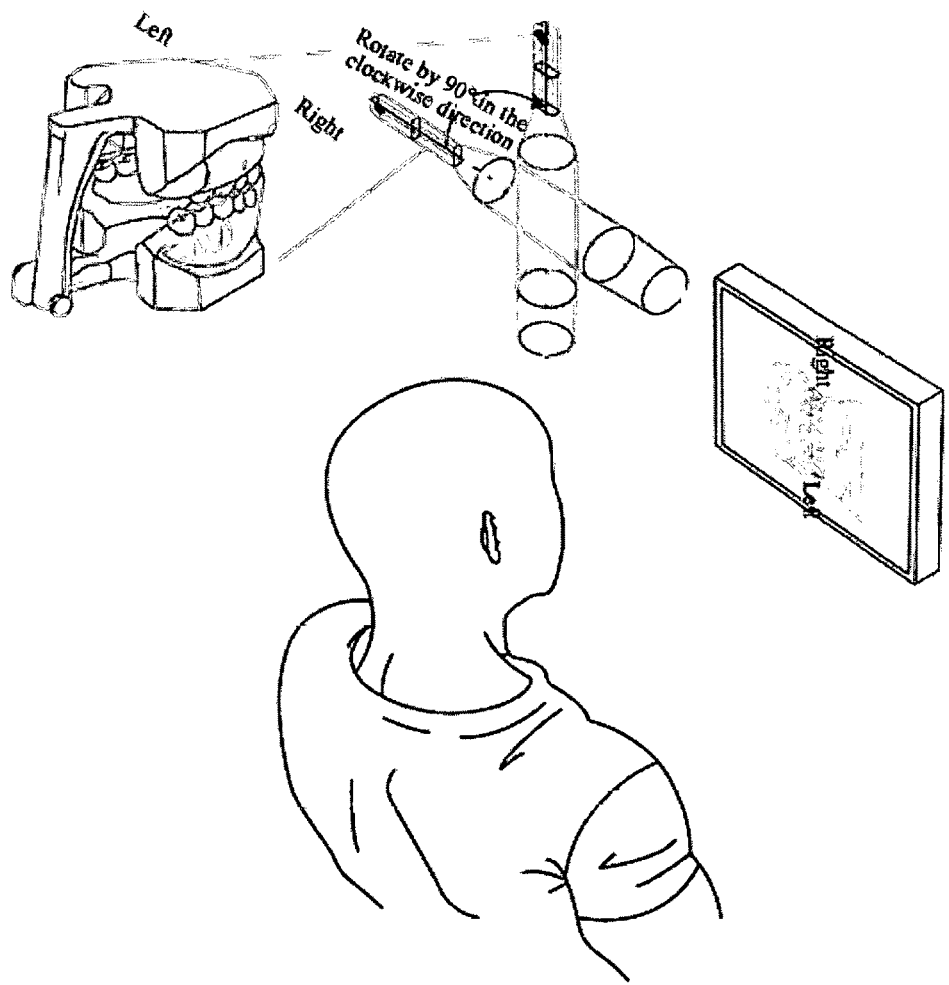
FIG. 2 is a sketch to use the endoscope in FIG. 1 moving in the clockwise direction by 90°.
Figure 3:
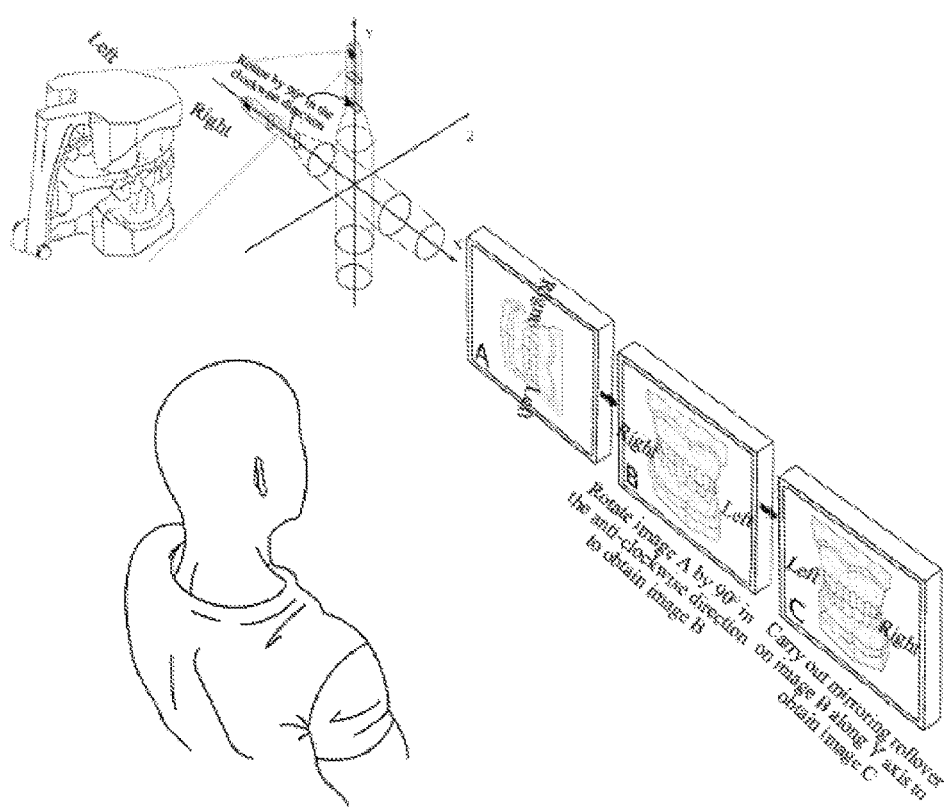
FIG. 3 is a sketch of a rollover image when the endoscope in the mode for private purpose of the invention moves in the clockwise direction by 90°.

FIG. 1 through FIG. 3 are sketches of the endoscope in the mode for private purpose.

FIG. 1 is a sketch to use an endoscope in the prior art. The left camera directly facing teeth of the endoscope horizontally is taken as the initial state of the endoscope. In the initial state of the endoscope, the display image and the image in which eyes look at teeth are in a 180° rotation state around Y axis. The display image and the image in which eyes look at a material object rotate from left to right by 180°, so that the image seen by the user and the image in which eyes look at real scenes are reversed, as a result, the operator cannot accurately operate the endoscope to the desired position due to direction moving errors when the endoscope is operated over a display screen.

On the basis of FIG. 1, the initial position of the oral endoscope in the prior art is moved by 90° horizontally in the clockwise direction, as shown in FIG. 2, the display image also moves by 90° in the clockwise direction with the moving speed and angle of the endoscope. In such case, the user cannot judge the actual position of the endoscope in the oral cavity while moving the endoscope, resulting in confusion of image judgment and operation of the material object.

FIG. 3 is an operation example of the endoscope of the invention. The endoscope moves by 90° horizontally in the clockwise direction from the initial position, each frame of display image is as shown in display device A, and each frame of image moved and corrected at opposite angles and at the same speed is as shown in display device B. Each frame of image subject to correction is subject to 180° mirroring rollover in the Y axis direction, and the final image is as shown in device C. At this point, the image displayed in the display screen and teeth are in mirroring display, and do not move with the endoscope, so that the user can judge the position of the endoscope in the oral cavity through the mirror image without confusion in the direction, and operate the endoscope more accurately and conveniently.

Figure 4:
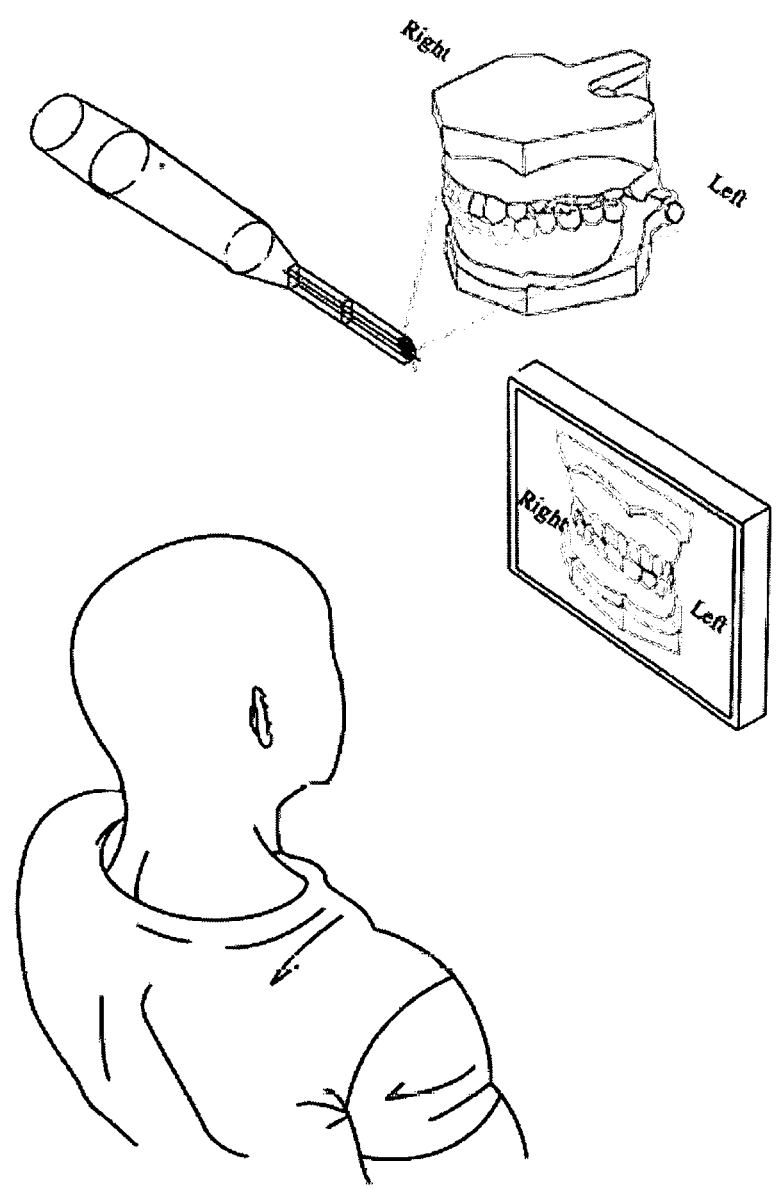
FIG. 4 is a sketch to use an endoscope for other purpose in the prior art.
Figure 5:
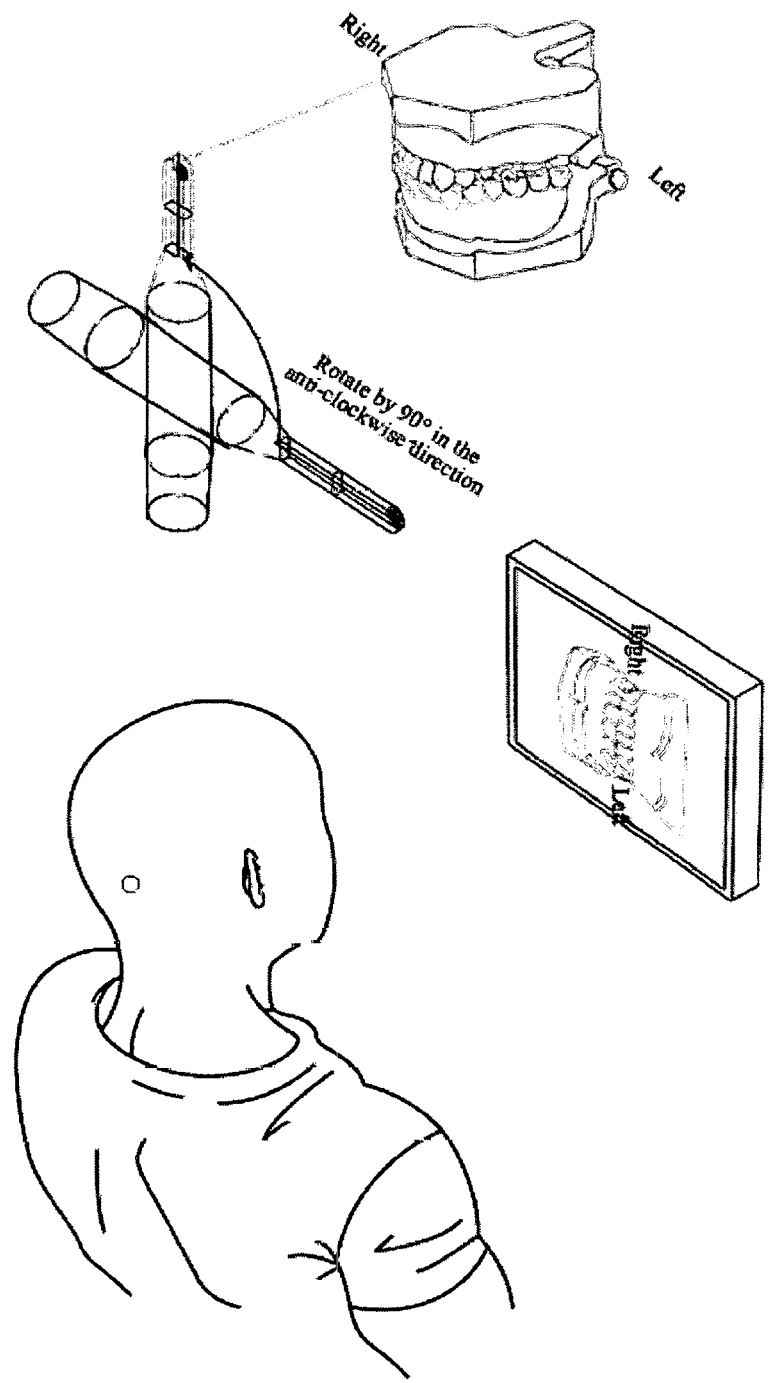
FIG. 5 is a sketch to use the endoscope in FIG. 4 moving in the anti-clockwise direction by 90°.
Figure 6:
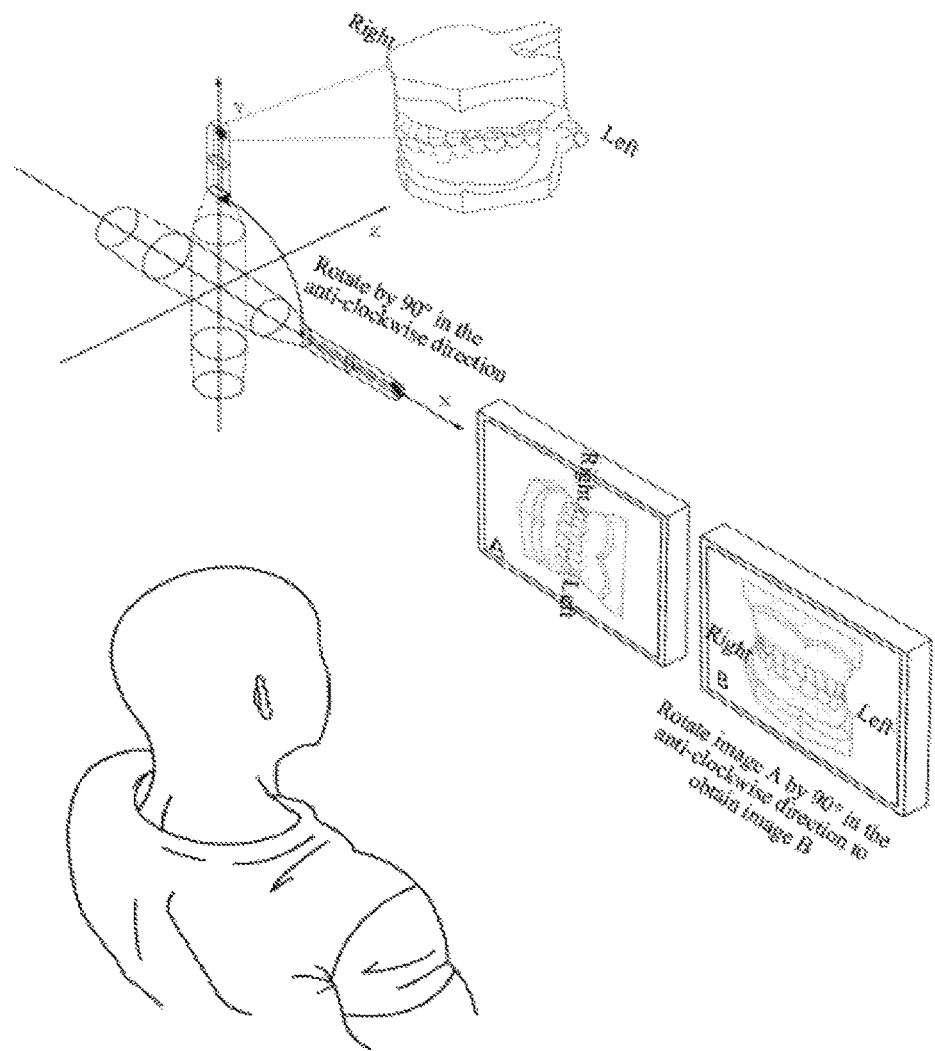
FIG. 6 is a sketch of a rollover image when the endoscope in the mode for other purpose of the invention moves in the anti-clockwise direction by 90°.

FIG. 4 through FIG. 6 are sketches of the endoscope in the mode for other purpose.

As shown in FIG. 4, the endoscope in the prior art and the subject oral cavity are in an initial state in which the left camera directly faces teeth horizontally. The image seen by an image viewer and the image in which eyes look at teeth are consistent without abnormality.

On the basis of FIG. 4, the endoscope rotates by 90° in the anti-clockwise direction in a perspective of the viewer from the initial state. As shown in FIG. 5, the display image rotates at the same speed in the clockwise direction in a perspective of the viewer. The rotating image disables the viewer to normally judge the position and situation of the endoscope in the oral cavity.

On the basis of operation in FIG. 4, movement of the endoscope generates the problem in FIG. 5, the endoscope rotates by 90° in the anti-clockwise direction in a perspective of the viewer from the initial state, and the display image rotates at the same speed in the clockwise direction in a perspective of the viewer. According to the problem in FIG. 5, the invention judges the sensor based on the position and speed of the endoscope, and confirms the moving position and speed of the endoscope, then moves and corrects each frame of image at the same moving angle and speed as the endoscope, as shown in FIG. 6, the display image does not move with the rotation of the endoscope, so that the viewer can view the displayed image like human eyes, and conveniently operate the endoscope at the same position as the endoscope without confusion.

The invention has the following beneficial effects:
The invention creatively solves the problem that it is difficult to positively display images acquired by oral endoscopes to subjects in the prior art, improving the operation accuracy of oral cavities, and improving the operation flexibility and shape design flexibility of endoscopes while ensuring the image display accuracy, thus the invention has good application values.

The invention claimed is:
1. An oral endoscope detection system, comprising: an insertion portion, a camera unit arranged on the insertion portion, a displacement information acquisition module, an operating mode setting module, a signal transmission module, an operation unit connected with the insertion portion, an image control processing module, and a display device,
wherein the camera unit, the displacement information acquisition module, the operating mode setting module, and the signal transmission module are connected to the image control processing module, and the display device is connected to the signal transmission module, wherein:

the operating mode setting module is configured to set a current operation mode to a first mode for examining a user's oral cavity or a second mode for examining an oral cavity of a subject other than the user;

the image control processing module stores information of standard initial attitude coordinate systems of the first mode and the second mode, wherein a standard initial attitude coordinate system of the first mode comprises an X-axis having a positive direction parallel to a straight line extending from the left shoulder to the right shoulder of the user, a Z-axis perpendicular to the X axis and having a positive direction pointing toward the user's oral cavity, and a Y-axis perpendicular to the X-axis and the Z-axis and having a positive direction pointing toward the upper part of the user's oral cavity, and an origin located on a connecting line connecting the operation unit and the camera unit, wherein a standard initial attitude coordinate system of the second mode comprises an X-axis having a positive direction parallel to a straight line extending from the left shoulder to the right shoulder of the subject, a Z-axis perpendicular to the X axis and having a positive direction pointing toward the subject's oral cavity, and a Y-axis perpendicular to the X-axis and the Z-axis and having a positive direction pointing toward an upper part of the subject's oral cavity, and an origin located on a connecting line connecting the operation unit and the camera unit, wherein, during operation, the insertion portion enters an oral cavity and moves in the oral cavity, the camera unit acquires an image of the subject oral cavity and transmits the image to the image control processing module, when the camera unit moves, the standard initial attitude coordinate system of the first mode or the second mode moves with the camera unit and becomes a standard attitude coordinate system of the first mode or the second mode, respectively, the displacement information acquisition module detects a rotation angle and a rotation rate of the connecting line between the camera unit and the operation unit relative to a rotation of the standard attitude coordinate system from X axis to Y axis during the acquisition of the image, the image control processing module corrects the image according to the current operation mode, the standard initial coordinate system corresponding to the current operation mode, the rotation angle and the rotation rate acquired by the displacement information acquisition module, the signal transmission module transmits signals to the image control processing module, and the display device displays corrected images.

2. The oral endoscope detection system according to claim 1, wherein, in the first mode, the step of correcting images by the image control processing module comprises:

step 1: correcting the image by applying to the image an same rotation rate and an opposite rotation angle; and step 2: carrying out 180° mirroring rollover on the corrected images obtained from the step 1.

3. The oral endoscope detection system according to claim 1, wherein, in the second mode, the image control processing module corrects the image by applying to the image a same rotation rate and a same rotation angle.

4. The oral endoscope detection system according to claim 1, wherein the signal transmission module comprises a wireless transceiver component or a USB wired transmission component.

5. The oral endoscope detection system according to claim 1, wherein the displacement information acquisition module is selected from the group consisting of an acceleration sensor, an angular velocity sensor, a gravity sensor, a gyroscope, and combinations thereof.

6. The oral endoscope detection system according to claim 1, wherein a central axis of the insertion portion is a connecting line between the camera unit and the operation unit.

7. A detection method of the oral endoscope detection system according to claim 6, comprising:

S1: selecting an operating mode by using the operating mode setting module;

S2: aligning the camera unit with the oral cavity, acquiring the image using the camera unit, and detecting the rotation angle and the rotation rate of the connecting line between the camera unit and the operation unit relative to rotation of the standard attitude coordinate system from X axis to Y axis by the displacement information acquisition module during shooting of the image;

S3: transmitting the image and the corresponding rotation angle and rotation rate to the image control processing module;

S4: correcting the images by the image control processing module;

when in the first mode, the step of correcting images by the image control processing module comprising:

step 1: correcting the image by applying to the image a same rotation rate and an opposite rotation angle; and step 2: carrying out 180° mirroring rollover on the corrected images obtained from step 1;

when in the second mode, correcting the image by applying the same rotation rate and the same rotation angle; and S5: displaying the image using the display device.

8. The oral endoscope detection system according to claim 2, wherein the signal transmission module comprises a wireless transceiver component or a USB wired transmission component.

9. The oral endoscope detection system according to claim 3, wherein the signal transmission module comprises a wireless transceiver component or a USB wired transmission component.

10. The oral endoscope detection system according to claim 2, wherein the displacement information acquisition module is selected from the group consisting of an acceleration sensor, an angular velocity sensor, a gravity sensor, a gyroscope, and a combination thereof.

11. The oral endoscope detection system according to claim 3, wherein the displacement information acquisition module is selected from the group consisting of an acceleration sensor, an angular velocity sensor, a gravity sensor, a gyroscope, and a combination thereof.

* * * * *